United States Patent [19]

Njemanze

[11] Patent Number: 5,121,744
[45] Date of Patent: Jun. 16, 1992

[54] PHYSIOLOGICAL G-SUIT MODULATOR

[76] Inventor: Philip C. Njemanze, 1436 F Stoney Meadows Dr., Valley Park, Mo. 63088

[21] Appl. No.: 633,037

[22] Filed: Dec. 21, 1990

Related U.S. Application Data

[63] Continuation-in-part of Ser. No. 384,435, Jul. 25, 1989, abandoned.

[51] Int. Cl.[5] ................................................ A61F 5/37
[52] U.S. Cl. .................................. 128/202.11; 600/19; 600/20
[58] Field of Search ...................... 128/202.11, 201.22, 128/202.12, 202.13, 200.24, 201.29, 202.19, 205.26, 661.07, 661.08, 661.09, 662.04, 662.01, 204.22, 204.23, 204.29; 600/19, 20; 364/510, 558, 434; 340/945, 611, 591, 626

[56] References Cited

U.S. PATENT DOCUMENTS

| | | | |
|---|---|---|---|
| 3,780,723 | 12/1973 | Van Patten et al. | 600/19 |
| 4,534,338 | 8/1985 | Grosbie et al. | 600/19 |
| 4,906,990 | 3/1990 | Robinson | 340/945 |

Primary Examiner—Richard J. Apley
Assistant Examiner—Glenn E. Richman

[57] ABSTRACT

A physiological antigravitational system for use in modern avionics to prevent a pilot from becoming unconscious, or developing related conditions, and includes a crew member G-suit for use for pressurization of the crew during flight, the suit incorporating a pressurization source for use with the G-suit for varying the degree of pressure generated within it during application, a controller microcomputer that regulates the varying of the pressurization source during flight, based on monitored changes in cerebral blood flow velocity, and force detectors responsive to the G-forces and operatively associated with the microcomputer to provide signals requiring variations in pressures generated from the pressurization source within the suit.

9 Claims, 6 Drawing Sheets

PHYSIOLOGICAL G-SUIT MODULATOR

CROSS-REFERENCE TO RELATED APPLICATION

This application is related to and comprises a continuation-in-part of the patent application filed by the same inventor on Jul. 25, 1989, under Serial No. 07/384,435, now abandoned, both of said applications being owned by a common assignee.

BACKGROUND OF THE INVENTION

This invention is related to systems for life support in avionics, in particular adjusting the anti-G suit and avionics antigravity system to prevent loss of consciousness, and also for crew member workload assessment.

Modern high performance aircraft and spacecraft operate at very high altitudes and acceleration rates. This may result to the effects of $+Gz$ forces that exceed human tolerance levels, leading to G-force induced loss of consciousness (G-LOC). G-LOC results from critical reduction in cerebral blood flow. Acceleration may also affect vision at high G's. The effect of acceleration on vision depends on the direction of the force vector, $+Gz$ acceleration (eye balls down) results in dimming of vision, followed by "tunnel vision" loss of sight which begins on the periphery and gradually narrows down until macular (central) vision remains. On the other hand $-Gz$ acceleration (eyeballs up) results in diminished vision, redout (red vision), an increase in the time for the eyes to accommodate, and blurring or double of vision. This is followed by total blackout and then loss of consciousness. Other mild effects of gravitational forces include motion sickness and space adaptation syndrome.

The use of anti-G suits helps prevent these episodes, by applying pressure to the abdomen and lower extremities to restrict downward pooling of blood, and reduce the fall in cerebral blood flow. The inflation and deflation of the anti G-suit is controlled by valves. Air is filled into the bladders only at periods of high G's.

Usually anti G-suit valves, in use today are mechanically controlled, or inertial valves, providing pressurized air to the bladders at pressures proportional to acceleration. Electronic servo feedback mechanisms for quicker triggering of the anti-G valve as disclosed in U.S. Pat. No. 3,780,723, to Van Patten and U.S. Pat. No. 4,243,024, to Crosbie, et al. These documents use the rate of change of acceleration to set the threshold level for triggering the signal that initiates the inflation of the anti-G suit. U.S. Pat No. 4,336,590, to Jacq, et al. describes a microprocessor controlled anti-G suit valve that intitiates inflation of the air bladders on control stick movement indicating imminent high acceleration.

The patent to Robinson, No. 4,906,990, is upon an anti-G system failure detection, and shows means for regulating the pressure within a anti-G suit, for use in space flight. The patent to McStravick, et al, No. 4,817,633, discloses a light weight device to stimulate and monitor human vestibuloocular reflex. This device includes a helmet formed of a rigid shell, which is lined with various bladders that are subject to variations in pressure, for detecting degrees of acceleration, and for measuring head and eye movements, and their effects upon the neurosensory system of the wearer. The patent to McGrady, No. 4,799,476, discloses a univeral life support system, for use in air craft or space craft travel, and providing for variations in the transmission of gases and signals sent between the craft, and the seat in which the pilot sits, for providing input data to the life support control system of the air craft, to adapt the system to appropriate temperature and gas supply schedule The patent to Van Patten, No. 4,736,731, discloses a rapid acting electro-pneumatic anti-G suit control valve.

In addition, a book edited by Aaslid R, entitled "*Transcranial Doppler Sonography,*" and published by Springer, of Wien, New York, dated 1989, on pages 39 through 50, describes the principle applied to measurement of blood flow velocity in cerebral arteries.

All the existing systems initiate pressure adjustment based on the physical parameter—acceleration, without consideration of physiologic changes in the human organism. Most importantly, the changes in cerebral blood flow are not monitored, so reductions, leading to loss of consciousness are not taken into consideration. Another disadvantage of increasing pressure in the extremities without consideration of the state of cerebral blood flow, is that this may lead to excessive increase resulting in a condition where blood supply exceeds demand and overall inefficient blood-brain exchange. The latter is an abnormal condition which may impair cortical function.

It is therefore desirable to have a system that triggers the anti-G suit pressure changes based on the assessment of the physiologic condition of the crew member in response to the changing environment.

An advantage of this invention is to provide a system that allows for individual tolerance level, since acceleration can produce varying effects from one individual to the other. This is of course dependent on the peculiarities of physiologic regulatory systems especially for blood pressure and cerebral blood flow.

Another object of this invention is that it allows individual workload assessment of crew members.

SUMMARY OF THE INVENTION

The use of the G-suit in modern avionics helps to limit the effects of gravitation on humans during flight operation. These effects include most importantly changes in blood flow to the brain during flight operation. This might result in blackout or sudden incapacitation of human operators or passengers. This invention describes a system for physiological setting of the gravitational suit (G-suit) according to cerebral blood flow changes, maintaining a particular threshold limit for the percentage change in mean flow velocity in or to the brain vessels.

This invention relates to physiologic G-suit modulator, it comprises a Doppler ultrasound instrument (pulsed or continuous wave or both) with spectrum analyzer, one or two transducers, a microcomputer, terminals to G-suit, host control computer and an end-tidal $CO_2$ measuring instrument. The special embodiment of this invention is illustrated in the specification, it includes block diagram for the format of the instrumentation, and how the system functions is shown by way of example in an avionic system. The human involved will be referred to herein as an operator, by way of example. The operator is interfaced with the system by way of placing the transducer on the temporal bone, a pulsed Doppler to $2MH_z$ transducer will be used for this illustration. The temporal bone above the zygomatic arc provides an ultrasonic window to insonate the cerebral arteries The middle cerebral artery (MCA) will be chosen for this illustration. It must be pointed out that if extracranial arteries supplying blood to the brain (e.g. common carotid artery or its branches) can be chosen, then the continuous wave Doppler modality will be used. This also means that the frequency be altered according to vessel diameter. So there are three major interface methods:

a. transcranial with pulsed wave Doppler modality;
b. extracranial with continuous wave Doppler modality; and
c. trans-extracranial dual modality Doppler instrument.

The method of interface will be determeined by preference, use, operation conditions, etc. The spectrum analyzer allows a visual control of the Doppler shifted frequency, and also the audio signal helps evaluate the quality of vessel insonation.

After the interface has been completed, and all other necessary procedures for flight preparation finished, the system becomes operational before actual take off. There is first a registration of resting values. The threshold values of the mean flow velocity are expressed as percentage change with reference to resting values. Each percentage change of mean flow velocity in or to the brain vessels is calibrated against the gravitational force changes and operation mode of the G-suit. This is synchronized by the microcomputer and the host avionics computer control system.

To set these thresholds, individual characteristics must be taken into account. These include operator's physical assessment, type of avionics (including space crafts, and space workstions), and purpose of the mission. The microcomputer processes the data from the Doppler instrument in the following manner. First it calculates the mean flow velocity in the artery, as at rest ($V_{rest}$), and during the various flight lags ($v_{flight}$), and then percentage change (dV). The formulation provides:

$$dV = \frac{V_{flight} - V_{rest}}{V_{rest}} \times 100$$

dV is calibrated to the changes in G-forces, and adjusted for the operational mode of the G-suit. The aim is to maintain an upper and lower operational limit for the percentage change. The upper limit is to allow for example workload induced increased mean flow velocity and hypoventilation, and the lower limit for example reductions by hyperventilation. Other accessory units for assessment of end-tidal $C_2$ can be included into the system, especially for pilots. The percentage change of mean flow velocity is kept within constant limits in the brain by constant changes of the operational mode of the G-suit, in response to G-forces.

If the MCA is chosen then all data acquistion will be done from the flow velocities measured in the main stem of the MCA. The sample volume can be placed at a distance of 50 mm from the surface of the transducers. Two transducers can be fired alternately or simultaneously and taking measures to prevent interference, this will enable registration of the mean flow velocities from both left and right MCA's. By doing this, the operator's (e.g. pilot, astronaut, etc.) workload can also be assessed during flight. With increased workload corresponding to increased percentage change of mean flow velocity on both sides.

It is an object of this invention to provide a system for altering a crew member anti-G suit pressure and avionics anti-G system based on the changes in cerebral blood flow velocity measurements.

It is a further object of this invention to provide a method for the assessment the crew member workload.

These and other objects of the invention are accomplished by monitoring the cerebral blood flow velocity, and the end tidal $CO_2$ and the gravitational force. The pressure or gravitational force acting on the crew member is monitored by flight condition sensors, and feed to the avionics computer. The blood flow velocity to the brain is constantly measured by a Doppler ultrasound instrument with left and/or right transducers, which is then fed to a controller microcomputer. The microcomputer also receives input from the capnometer (measuring end-tidal carbon dioxide ($CO_2$)) and the G-force or pressure readings from the avionics computer.

The input data including, mean cerebral blood flow velocity (MBFV), end-tidal $CO_2$ and pressure, are constantly updated. The controller microcomputer continuously compares the in-flight MBFV to that measured at baseline and calculates the percentage change. This in turn is compared to stored threshold values. This controller microcomputer then uses that data input from the Doppler instrument, capnometer measurements, and G force readings from avionics computer to regulate the anti-G system. The latter comprises the anti-G suit pressure and aircraft acceleration system. This is accomplished by generation of "on" signal to adjust pressure until the desired MBFV is reached, and subsequent stabilization and an "off" signal at all times when the threshold values are not exceeded.

In addition, the percentage change in cerebral blood flow velocities in the middle cerebral arteries supplying the left and right hemispheres can be used to predict crew member work load. The latter is based on the observation that increasing workload induces a rise in cerebral blood flow velocity. The system calibrates percentage change in cerebral blood flow to a preset operational workload. The system can be physically attached to the avionics. This can also be attached to small mobile units like the manned maneuvering unit for use in space work stations. The entire system is powered by electricity from the avionics or a in case of the mobile units battery sources are used. Other modifications of this system include the use of transducers measuring blood flow velocity in the extracranial vessels supplying blood to the brain. And possible use of continous wave Doppler instrument. The system can be used for a one man avionics system or several crew members.

These and other objects may become more apparent to those skilled in the art upon reviewing the description of the invention as set forth hereinafter, in view of its drawings.

BRIEF DESCRIPTION OF THE DRAWINGS

FIG. 5 is a flow chart of the operations of the microcomputer used in conjunction with the values determired by the pressure suit and the avionics anti-G system in measuring cerebral blood flow velocity; and .

DESCRIPTION OF THE PREFERRED EMBODIMENT

Figure 1:
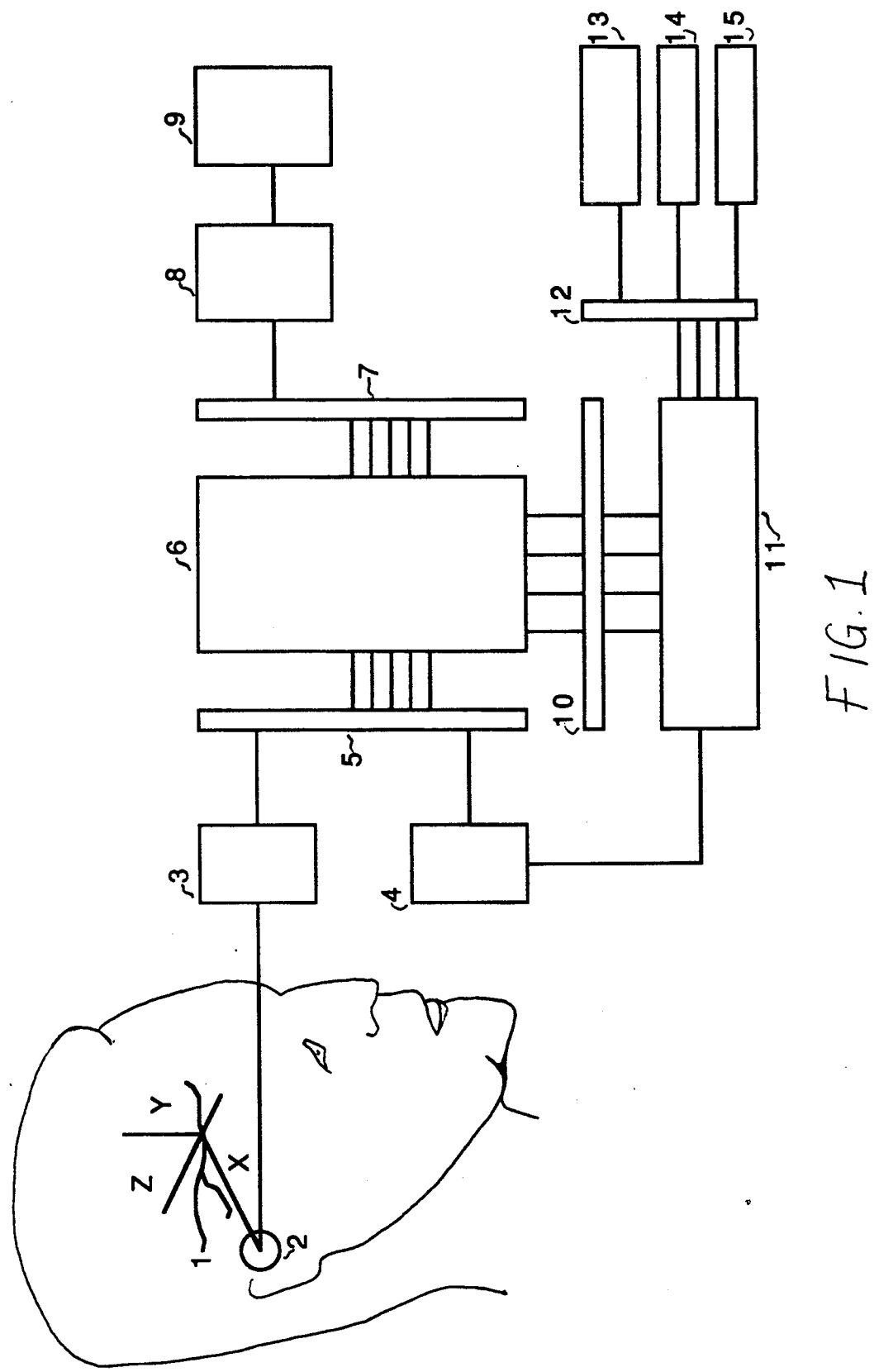
FIG. 1 illustrates in block diagram form, a physiologic antigravitational system in accordance with this invention.

A method for the physiologic control of anti-gravitational system is illustrated in FIG. 1. Doppler ultrasonic instrument 3 with transducer 2 generates analog Doppler shifted signal that corresponds to the speed of the erythrocytes moving in the main stem of the middle cerebral artery (MCA), as at 1, or any other major cerebral vessel as described by Aaslid. Such a Doppler ultrasonic instrument can be acquired from Eden Medical Electronics (EME) Company, of Uberlingen, Germany, Model Number is TC264. The frequency of this signal is proportional to the velocity of the moving erythrocytes. The sample volume can be guided by the x, y, and z coordinate location of the vessel, as above. This probe position has to be maintained constant by a fixation device. In this illustration using a pulsed Doppler instrument operating at 2 MHz the distance or range of the sample volume from the skin surface through the temporal bone to the vessel can be controlled. The Doppler shifted signal is converted to digital form and outputs the blood flow velocities (peak systolic, mean and end-diastolic) on a spectrum analyzer. Initially the controller microcomputer 6 receives the blood flow measurements through an interface 5 and stores it along with the capnometer 4 measurements of end-tidal $CO_2$, and also through the interface 10 the measurements of acting G-force or pressure read from the avionics computer 11. The microcomputer can be obtained from Intel Company, of San Jose, Calif., as Model No. 70,486. The avionics computer 11 can be obtained from McDonnell Douglas Corp. of St. Louis, Mo., Model No. MDC 281, or from Marconi Company, of Lincoln, England, Model No. MAS 281. All microprocessors used for this purpose must meet the military standard 1750. The $CO_2$ monitor can be obtained fom Datex Instrumentation Company, of Helsinki, Finland, Model No. 223. The latter receives information via an interface 12 from flight condition sensors for G-forces 13 and sends commands to the avionics acceleration system 15 and also displays operational information of system configuration on the monitor 14. The operator can set the threshold and baseline values. The percentage changes of cerebral blood flow velocities, for instance mean blood flow velocity (MBFV) that occurs in flight conditions are compared to set threshold values of measured parameters. If this exceeds the threshold, a signal is generated from the controller microcomputer 6 to the pressure altering device 8, in most cases G-suit valves and avionic acceleration control system 15. Prior to this the system checks the capnometer file for transient variations in MBFV due to respiration unrelated to changes in G forces. And then adjusts the pressure in the G-suit 9 and avionics acceleration control system 15. The pressure will be adjusted until the desired MBFV is attained and the system shuts off as in a feedback mechanism. In case the measured values lie within the normal limits, the system functions continually without changing pressure.

Figure 2:
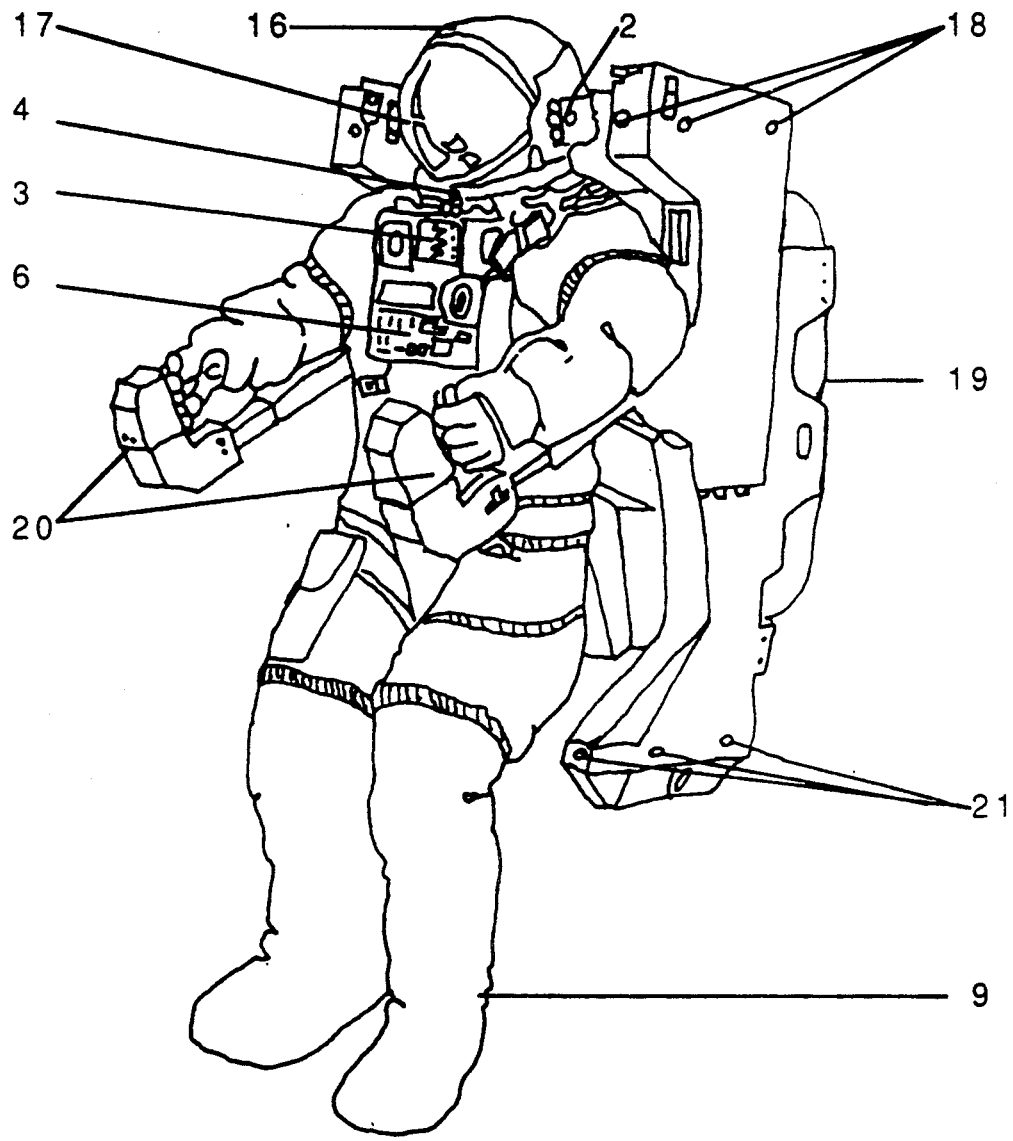
FIG. 2 is a diagram of the invention adapted to an anti-G suit in a manned maneuvering unit.

FIG. 2 illustrates in greater detail the physical appearance of a crew member in a typical space anti-G suit and a manned maneuvering unit, attached to the present invention. The suit 9 comprising a helmet 16, a protective visor 17 with the capnometer sensor 4 inserted into the breathing mask. The transducer 2 is connected to the Doppler instrument 3 with spectrum analyzer and the controller microcomputer 6 which controls the pressure in the space suit or extra-vehicular mobility unit 9 and the acceleration controls 20 of the manned maneuvering unit 19, with thruster nozzles shown at 18 and 21.

Figure 3:
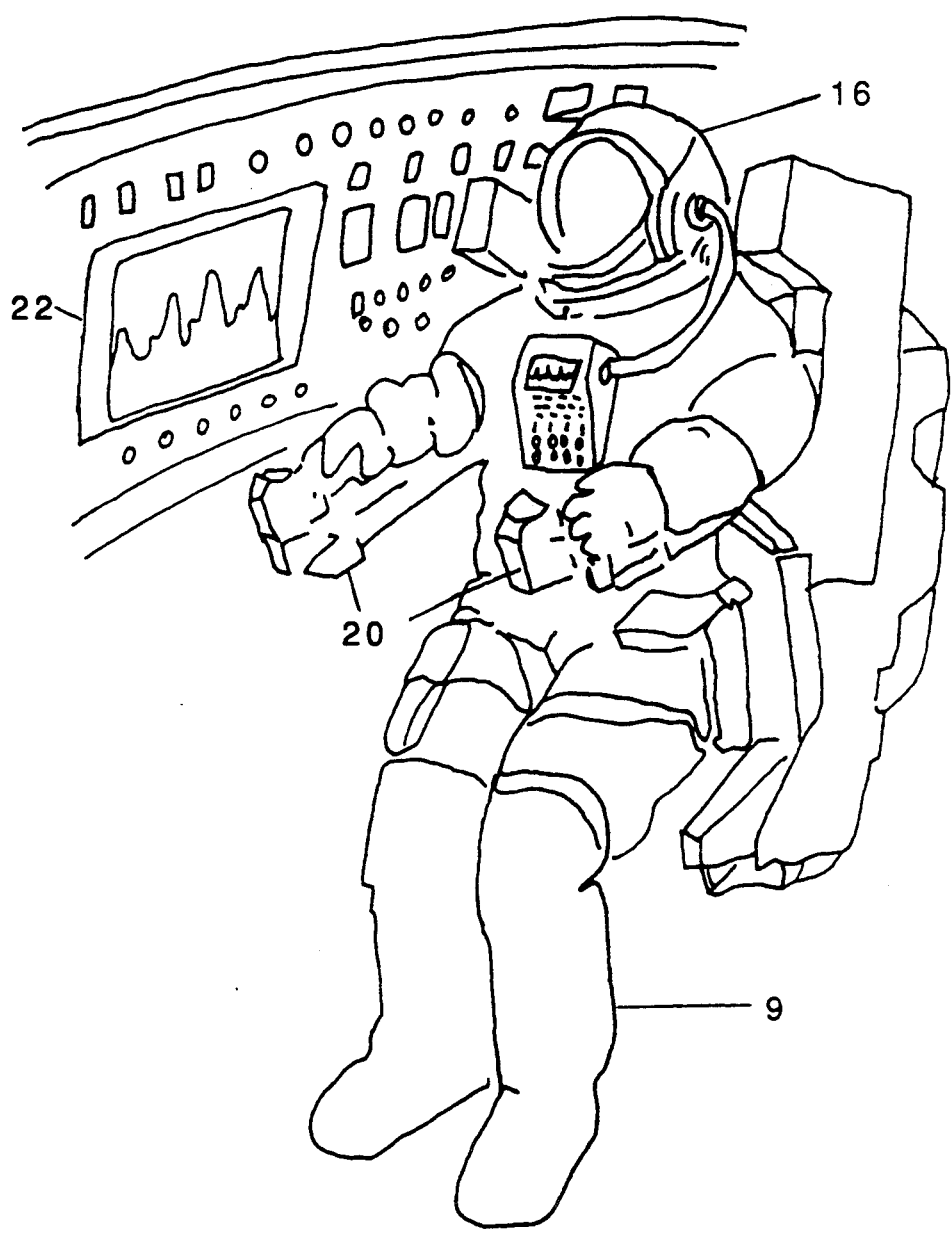
FIG. 3 is a diagram of an anti-G suit adapted for use in the spacecraft.

FIG. 3 shows the system attached to the space craft and displays information on a station based monitoring unit 22.

Figure 4:
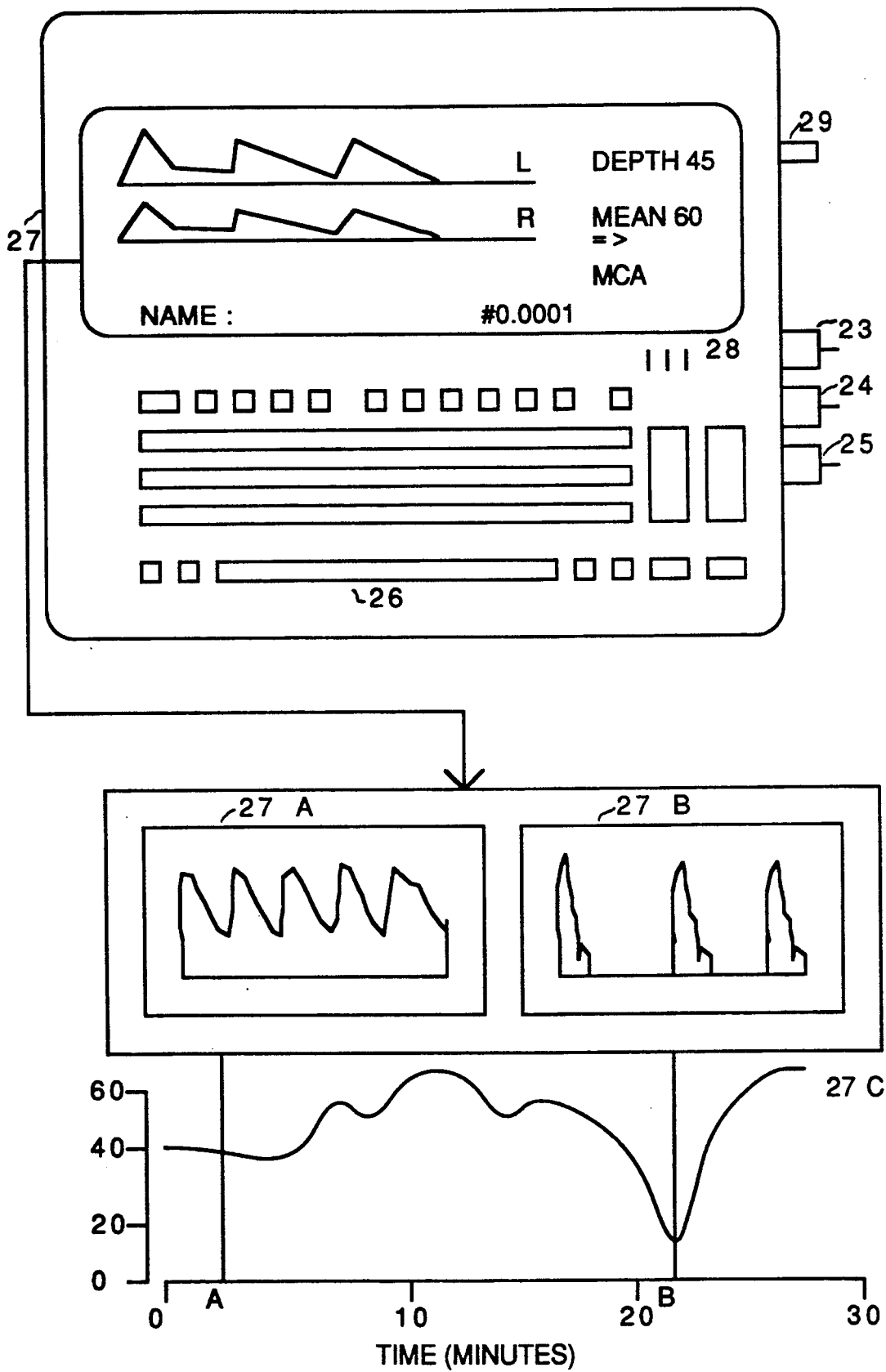
FIG. 4 is an illustration of output from the spectrum analyzer in conditions of baseline and during loss of consciousness.

FIG. 4 shows the Doppler instrument with spectrum analyzer 27 showing terminals for connections. Terminals refer to direct points of connection to other parts or instruments. The transducer terminal 29, that attaches the transducer 2, the anti-G suit terminal 23 connects to the G-suit system, capnometer terminal 24 connects both instruments, and avionic computer terminal 25 is the point of connection of both computers. The input into the controller microcomputer 6 can be performed through a keyboard 26. The adjustments of insonation parameters and spectral display can also be entered through the same keyboard 26. The output of the Doppler instrument comprises the spectral and audio signals. The audio signal can be heard on the loudspeaker 28, and the spectra displayed for example as shown for baseline measurements 27a and during unconsciousness, as displayed at 27b. The latter shows a reduction in MBFV by over 75% compared to baseline values during unconsciousness in this subject. The MBFV measurements shown in the curve 27c are for each cardiac cycle and represent the data entered into the controller microcomputer 6.

Figure 5:
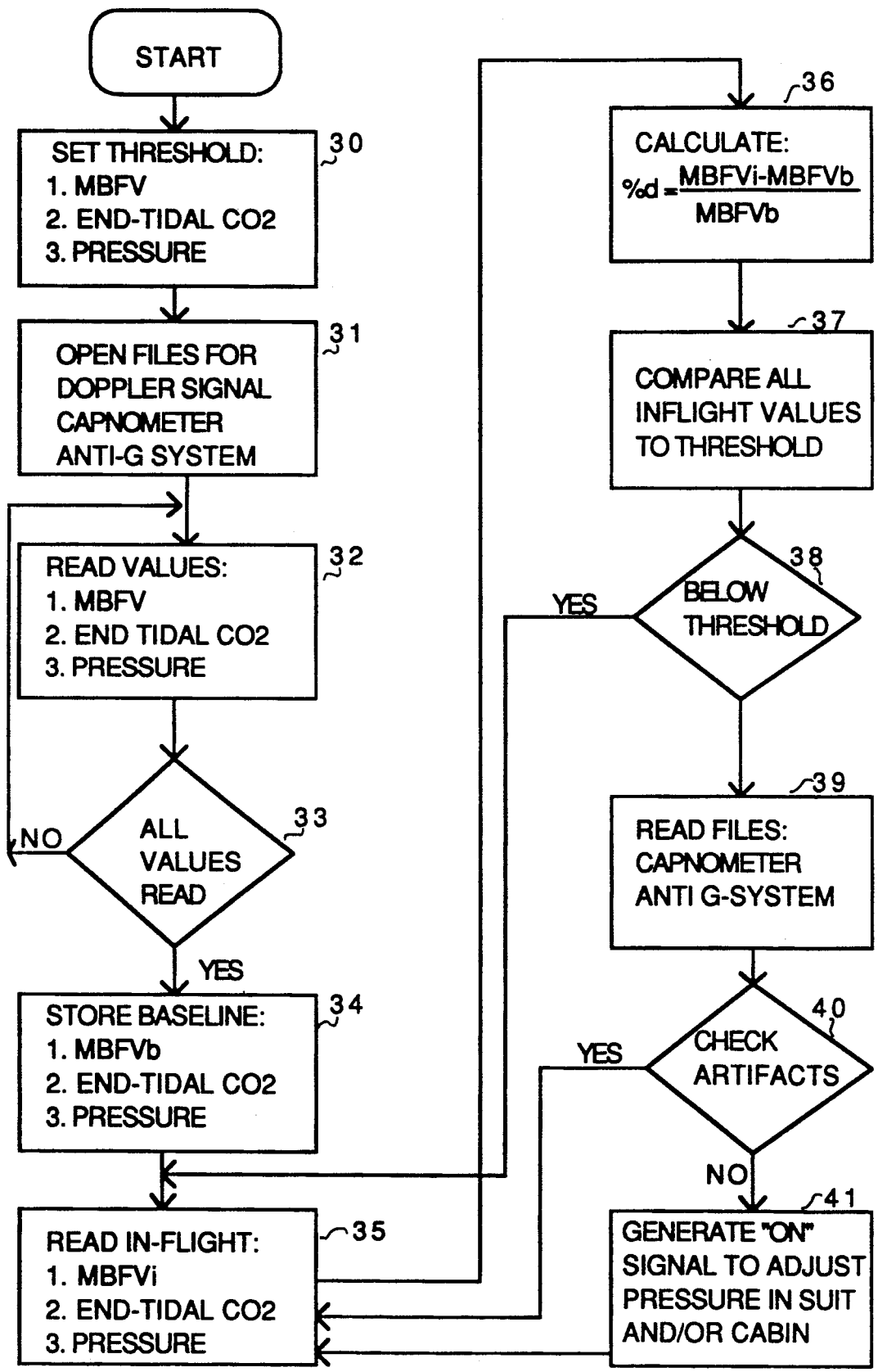

FIG. 5 shows the computer algorithm or flow chart for the functional operation of the controller microcomputer 6. All of the detected and collected data from all of the sources, such as the sensors 3, 4, and the avionics computer 11 are assembled in the microcomputer memory 30. In flight simulated conditions the MBFV, end-tidal $CO_2$ and pressure or G-force threshold values are determined and preset in the controller microcomputer and stored in the files 31. Immediately the system is set for flight it reads data from the Doppler instrument 3, capnometer 4 and pressure/force from avioncs computer 11, as shown in block 32. The system will proceed to the next stage if all data is read 33. In flight conditions the controller microcomputer measures baseline data (34) and continuously records instantaeous mean blood flow velocity (MBFVi), end-tidal $CO_2$ and pressure (G-forces) designated in 35. Using baseline data and measured MBFVi the controller computer calculates the percentage change (%d) in MBFV and compares this value to threshold as in 36. The microcomputer 6 compares the inflight data to that stored as threshold shown in 37. If this is within normal limits then the system does not generate any signal to adjust the pressure (38) In case the system detects a value greater than threshold it reads the capnometer measurements to confirm the absence of respiratory induced changes and also the presence of increase G-force of the anti-G monitoring system shown in block 39. There are subroutines that verifies the absence of other technical artifacts designated by 40. In the absence of the latter, the controller microcomputer generates a signal to adjust the pressure in the anti-G suit and to the avionic system configuration to alter cabin pressure, usually by adjusting acceleration (41). The pressure alteration discontinues when the desired MBFVi are reached.

In addition, the percentage change in cerebral blood flow velocities in the middle cerebral arteries supplying the left and right hemispheres can be used to predict crew member work load. The latter is based on the observation that increasing workload induce a rise in cerebral blood flow velocity. This is accomplished by using the amount of changes of cerebral blood flow velocity to the right and left cerebral hemispheres. At higher workload levels the cerebral blood flow velocity increases to meet neuronal metabolic demands. This provides an index of workload if it is known what tolerance limits of changes in cerebral blood flow velocity correspond to normal levels of workload. The latter can only determined for individual subjects by way of simulations of high, low and normal workload levels and determining the corresponding cerebral blood flow velocity in the right and left cerebral hemispheres. The system calibrates percentage change in cerebral blood flow to a present operational workload.

The system can be physically attached to the avionics. This can also be attached to small mobile units like the manned maneuvering unit for use in space work stations. The entire system is powered by electricity from the avionics or in case of the mobile units battery sources are used. Other modifications of this system include the use of transducers measuring blood flow velocity in the extracranial vessels supplying blood to the brain. And possible use of continuous wave Doppler instrument. The system has been described by a one man avionic system, but can be used for a number of crew members the same avionics. In which case, changes in avionic system configuration is based on detection of abnormal changes in several crew members, otherwise changes are limited to pressure adjustments in anti-G suit.

Figure 6:
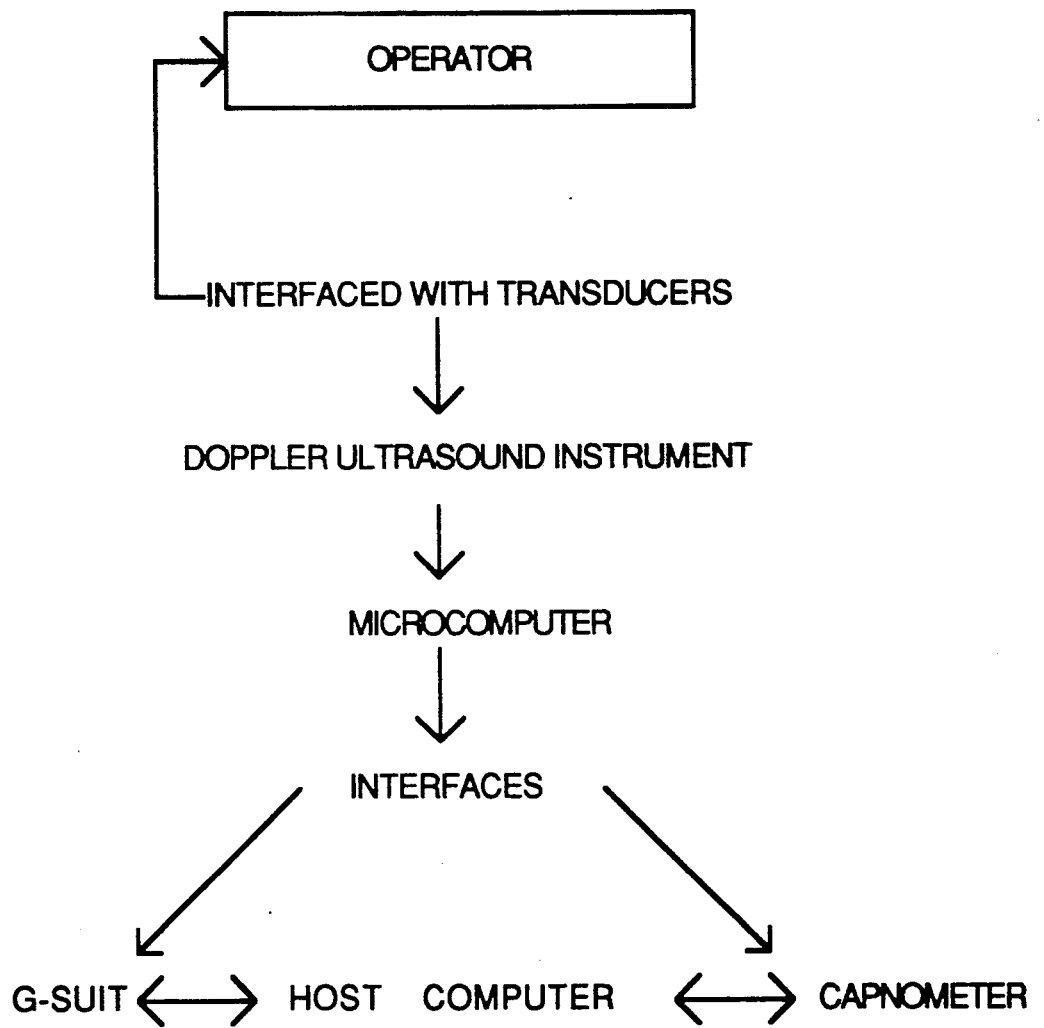
FIG. 6 is a flow chart of the instrumentation operations.

As previously summarized, FIG. 6 is the flow chart of the block diagram of the instrumentation. The operator involved is interfaced with the system by way of placing the transducers upon him, as noted, in the manner as previously reviewed, and a pulsed Doppler transducer is used for the illustration. The signals from the transducer are then delivered to the Doppler U.S. 3, and then, conducted to the microcomputer, and the microcomputer 6 is connected through the interfaces 5, 7, and 10, to the pressure altering device 8 of the G-suit, the host computer 11, and to the capnometer 4.

The Doppler signal obtained with transducer 2 and instrument 3 delivers the MBFV measurments to the controller microcomputer 6, the latter by way of interfaces 5, 7, and 10 receives data from the capnometer 4, about the pilot ventilation, and from the avionics computer 11 about G-forces, and communicates the needed pressure adjustment of the G-suit 9 via its pressure setting system 8. The arrow direction show predominant controlling unit As can be noted, the host avionic computer though sends infomration to the microcomputer, the operational control is exerted by the latter. The capnometer 4, communicates with the host avionic computer as a means of regulating the ventilation environment of the avionics. Also, the host avionic computer communicates with the G-suit, to sense the pressure levels in stationed systems as a backup for the microcomputer/G-suit interface.

Other variations or modifications to the subject matter of this invention, in light of what has been disclosed herein, may occur to those skilled in the art upon review of the subject matter of this invention. Such variations or modifications, if within the spirit of this invention, are intended to be encompassed within the scope of any claims to patent protection issuing upon this development. The description of the preferred embodiment set forth herein is done so for illustrative purposes only.

Having thus described the invention, what is claimed and desired to be secured by Letters Patent is:

1. A physiological antigravitational system for use in modern avionics to prevent unconsciousness and related conditions by way of monitoring cerebral blood flow velocity and using that information to alter anti-G pressure with a wide variety of applications dependent upon the mission and the type of avionics involved, said system comprising:

a crew member G-suit for use during flight, a pressurization source for use with the G-suit for varying its established pressure during application, a controller microcomputer that regulates the varying of the pressurization source used with the crew member G-suit and avionics system, and force/pressure detectors responsive to the generated G-forces and operatively associated with the microcomputer to provide various signals thereto for varying the pressure generated from the pressurization source and means for measuring cerebral blood flow velocity of the crew member during flight, said means for measuring cerebral blood flow velocity comprising a Doppler instrument and spectrum analyzer incorporating transducers for providing blood flow measurements.

2. The invention of claim 1 and further including means for measuring the respiratory activity of a crew member during flight, and communication means deriving signals responsive to the respiratory activity and delivering said signals to the microcomputer for varying the pressurization source.

3. The invention of claim 1 and including means responsive to the signals generated from the anti-G suit pressure measurements for adjustment and regulation of the pressure detected to command the microcomputer to vary the Pressure within the G-suit from its pressurization source to compensate for variations and pressures varying from the normal pressure desired for the crew member.

4. The invention of claim 1 and further including electrical power means provided for the avionic system, and said power force providing electrical charge to the system during its operations.

5. The invention of claim 1 and using the blood flow velocity parameter for adjusting the avionic settings of the means for providing flight.

6. A physiological G-suit modulator which comprises, a G-suit for the crew member, a Doppler instrument incorporating spectrum analyzer which is operated by a wave form of one of a pulse or continuous wave, transducer means operatively associated with the spectrum analyzer, a microcomputer responsive to the signals received by the transducers, terminal means operative with the G-suit modulator, and a host control computer system responsive to the microcomputer, and an end-tidal $CO_2$ measuring instrument responsive to the terminals for the G-suit for detecting the mean flow velocity of the blood supply in the vessels of the crew member, for determining gravitational effects upon the crew member, and to provide for compensation, through the operations of the microcomputer, for variations in the pressure maintained within the G-suit for the crew member.

7. The invention of claim 6 and including evaluation means provided with the G-suit modulator and for evaluating the mean flow velocity of the blood flow within the cerebral hemispheres of the crew member for determining G-forces imposed upon the crew member during flight operations.

8. The invention of claim 6 and including evaluation means provided with the G-suit modulator and for evaluating the mean flow velocity of the blood flow within intra-extracranial vessels of the crew member for determining G-forces imposed on the crew member during high or low altitude operations.

9. The invention of claim 6 and including evaluation means of using the detected percentage change in cerebral blood flow velocity in the right and/or left hemisphere to estimate a crew member workload by comparing the inflight measured changes to set thresholds, and using established limits to determine the level of workload.

* * * * *